(12) United States Patent
Thotla et al.

(10) Patent No.: US 12,006,285 B2
(45) Date of Patent: Jun. 11, 2024

(54) METHOD FOR PURIFYING ISOBUTENE FROM A C4 STREAM AND PROCESS SYSTEM THEREFOR

(71) Applicants: OMV Downstream GmbH, Vienna (AT); BASF SE, Ludwigshafen (DE)

(72) Inventors: Suman Thotla, Mannheim (DE); Pawel Tadeusz Czajka, Mannheim (DE); Stefan Manfred Iselborn, Frankenthal (DE); Kai-Uwe Wemhöner, Vienna (AT); Jürgen Popp, Vienna (AT)

(73) Assignees: OMV DOWNSTREAM GMBH, Vienna (AT); BASF SE, Ludwigshafen (DE)

( * ) Notice: Subject to any disclaimer, the term of this patent is extended or adjusted under 35 U.S.C. 154(b) by 0 days.

(21) Appl. No.: 18/116,336

(22) Filed: Mar. 2, 2023

(65) Prior Publication Data

US 2023/0202948 A1    Jun. 29, 2023

Related U.S. Application Data

(63) Continuation of application No. 17/265,472, filed as application No. PCT/EP2019/070859 on Aug. 2, 2019, now Pat. No. 11,649,197.

(30) Foreign Application Priority Data

Aug. 2, 2018   (EP) ..................... 18187133

(51) Int. Cl.
*C07C 5/25*   (2006.01)
*B01D 3/00*   (2006.01)
(Continued)

(52) U.S. Cl.
CPC ............ *C07C 5/2556* (2013.01); *B01D 3/007* (2013.01); *B01D 3/143* (2013.01); *B01J 21/04* (2013.01);
(Continued)

(58) Field of Classification Search
CPC ......... C07C 5/2556; C07C 7/005; C07C 7/04; C07C 7/148; C07C 7/14841;
(Continued)

(56) References Cited

U.S. PATENT DOCUMENTS 4,255,605 A   3/1981  Dixon
4,410,754 A   10/1983 Gewartowski
(Continued)

FOREIGN PATENT DOCUMENTS

CN   1226227 A     8/1999
CN   101885660 A   11/2010
(Continued)

OTHER PUBLICATIONS

Doherty et al. ("Distillation." Chap 13.0 in Perry's Chemical Engineer's Handbook. 7th Ed., 2008) (Year: 2008).*
(Continued)

*Primary Examiner* — Youngsul Jeong
*Assistant Examiner* — Jason Y Chong
(74) *Attorney, Agent, or Firm* — NIXON & VANDERHYE P.C.

(57) ABSTRACT

A process for the purification of isobutene from a C4 stream with at least 1-butene, 2-butene, isobutane and isobutene includes isomerizing 1-butene from a stream of material which is concentrated in isobutane and isobutene obtained from the C4 stream into 2-butene, using a catalyst in an isomerization reactor; supplying a product stream from the isomerization reactor to a rectification column; and providing a stream of material which is concentrated in isobutene. A processing facility is utilized for the purification of isobutene from the C4 stream.

4 Claims, 4 Drawing Sheets

(51) Int. Cl.
  *B01D 3/14*    (2006.01)
  *B01J 21/04*   (2006.01)
  *B01J 23/42*   (2006.01)
  *B01J 23/44*   (2006.01)
  *C07C 7/00*    (2006.01)
  *C07C 7/04*    (2006.01)

(52) U.S. Cl.
  CPC .............. *B01J 23/42* (2013.01); *B01J 23/44* (2013.01); *C07C 7/005* (2013.01); *C07C 7/04* (2013.01); *C07C 2521/04* (2013.01); *C07C 2523/42* (2013.01); *C07C 2523/44* (2013.01)

(58) Field of Classification Search
  CPC ............ C07C 2521/04; C07C 2523/42; C07C 2523/44; C07C 11/08; C07C 11/09; B01D 3/007; B01D 3/009; B01D 3/143; B01J 21/04; B01J 23/42; B01J 23/44; B01J 8/00; Y02P 20/10
  See application file for complete search history.

(56) References Cited

U.S. PATENT DOCUMENTS

| | | | | |
|---|---|---|---|---|
| 4,555,312 | A * | 11/1985 | Ogura | C07C 7/08 585/860 |
| 4,777,322 | A * | 10/1988 | Hoelderich | C07C 5/2537 585/666 |
| 5,536,887 | A | 7/1996 | Minkkinen et al. | |
| 6,215,036 | B1 | 4/2001 | Dorbon et al. | |
| 6,242,661 | B1 * | 6/2001 | Podrebarac | C07C 7/148 208/138 |

FOREIGN PATENT DOCUMENTS

| | | |
|---|---|---|
| DE | 198 01 089 | 7/1998 |
| EA | 020352 | 10/2014 |
| EP | 0 922 018 | 9/2000 |
| EP | 1 200 378 | 1/2005 |
| EP | 2 170 494 | 8/2011 |
| GB | 570692 | 7/1945 |
| JP | 47-13251 | 4/1972 |
| JP | 10-182507 | 7/1998 |
| JP | 2001-506229 | 5/2001 |
| JP | 2003-505353 | 2/2003 |
| KR | 10-2000-0029848 | 5/2000 |
| KR | 10-2002-0029083 | 4/2002 |

OTHER PUBLICATIONS

International Search Report dated Sep. 18, 2019 issued in PCT International Patent Application No. PCT/EP2019/070859, 5 pp.
European Search Report dated Feb. 1, 2019 issued in European Patent Application No. 18187133.6, 9 pp.
Japanese Office Action dated May 17, 2022 issued in Japanese Patent Application No. 2021-505726 and English Translation, 8 pp.
Korean Office Action dated Jan. 31, 2023 issued in Korean Patent Application No. 10-2021-7006195 and English Translation, 18 pp.
Russian Office Action dated Jul. 29, 2021 issued in Russian Patent Application No. 2021103504/04(007582) and English translation, 23 pp.
Sinnott ("2.14 Recycle Processes." Chemical Engineering Design, Fourth ed. vol. 6, 2005, 50). (Year: 2005).
Chinese Office Action dated Mar. 3, 2023 issued in Chinese Patent Application No. 2019800514877 and English translation, 22 pp.

* cited by examiner

METHOD FOR PURIFYING ISOBUTENE FROM A C4 STREAM AND PROCESS SYSTEM THEREFOR

CROSS-REFERENCES TO RELATED APPLICATIONS

This application is a continuation of U.S. patent application Ser. No. 17/265,472, filed Feb. 2, 2021, pending, which is the U.S. national phase of PCT International Application No. PCT/EP2019/070859, filed Aug. 2, 2019, which designated the U.S. and claims priority to European Patent Application No. 18187133.6, filed Aug. 2, 2018, the entire contents of each of which are hereby incorporated by reference in this application.

BACKGROUND

The invention relates to a process and a processing facility for the purification of isobutene from a C4 stream which comprises at least 1-butene, 2-butene, isobutane and isobutene.

Purity requirements for isobutene as a starting material for various products are continuously increasing. Particular purity is required, for example, when isobutene is used as a raw material for the production of isobutene-containing plastics. In these production processes, in general, purity requirements for the starting material are specified such as, for example, the minimum isobutene content, as well as the maximum content for 1-butene and other components such as butane. C3 and C5 hydrocarbons. A particular challenge is posed in the production of products which are concentrated in isobutene from a C4 stream which comprises different hydrocarbons containing 4 carbon atoms per molecule such as, for example, 1-butene, 2-butene, isobutane and isobutene, namely the separation of isobutene and 1-butene, because the boiling points of isobutene and 1-butene are very close together, whereupon a separation with the aid of distillation is only possible with a relatively high energy consumption. In contrast, the separation of isobutene and 2-butene is easier because of the larger difference between the boiling points of these two butene compounds. Thus, processes are known in the prior art which are essentially based on the fact that 1-butene in the C4 stream is isomerized to 2-butene in order to facilitate the separation of isobutene from the C4 stream.

Thus, GB 570 692 discloses a process for separating isobutene in which essentially, a C4 stream which contains isobutene and 1-butene is brought into contact with a catalyst which accelerates the isomerization of 1-butene to 2-butene at a space velocity which is high enough to transform 1-butene into 2-butene but not isobutene, and isobutene is obtained by fractionation. In order to increase the purity of the isobutene in the product stream of the process, the catalytic isomerization in a reactor and the fractionation in a rectification column can be repeated, however this significantly increases the energy consumption of the production process. Furthermore, disadvantageously, the purity of the isobutene produced using that process is too low for numerous applications, because the mass fraction of 1-butene after the isomerization is too high to obtain the necessary purity of the isobutene in the subsequent fractionation, since the 1-butene has been concentrated in the isobutene-containing product stream.

EP 0 922 018 B1 discloses a process for the production of isobutene from a C4 stream which contains isobutene and 1-butene. In that process, the C4 stream is treated in a distillation column, wherein a portion of the liquid flowing in the distillation column is removed from the distillation column and supplied to a reactor for isomerizing 1-butene to 2-butene. In the reactor, with the aid of a catalyst, the isomerization of 1-butene to 2-butene is preferred over the isomerization of isobutene. However, disadvantageously, the purity of the isobutene in the product stream is too low for specific further uses of the product stream.

SUMMARY

An objective of the described embodiments is to alleviate or overcome at least individual disadvantages of known processes for the purification of isobutene from a C4 stream. In particular, the aim of the described embodiments is to provide a process and a processing facility for the efficient purification of isobutene from a C4 mixture or to obtain the highest possible degrees of isobutene purity.

The described embodiments provide a process for the purification of isobutene from a C4 stream which comprises at least 1-butene, 2-butene, isobutane and isobutene, in which at least the following steps are carried out:

supplying a stream of material which is concentrated in isobutane and isobutene obtained from the C4 stream and a stream of hydrogen to an isomerization reactor, wherein the isomerization reactor comprises a catalyst which comprises at least one metal which is active in hydrogenation on a support, preferably an aluminium oxide support;

bringing the stream of material which is concentrated in isobutane and isobutene and the stream of hydrogen into contact with the catalyst in the isomerization reactor, whereupon 1-butene present in the stream of material which is concentrated in isobutane and isobutene is isomerized to 2-butene;

supplying a product stream which comprises less 1-butene in relation to the stream of material which is enriched with isobutane and isobutene from the isomerization reactor to a rectification column; and providing a stream of material which is concentrated ire isobutene:

by separating this stream of material:

via a side stream from the rectification column, or via a side stream and as the bottom product from the rectification or as a bottom product from the rectification column, wherein furthermore, a stream of material which is concentrated in isobutane is separated from the rectification column as the overhead product, or in which an overhead product from the rectification column that is concentrated in isobutane, which contains isobutene in addition to the isobutane, is supplied to a second rectification column in order to separate the isobutane from the isobutene, and to obtain the stream of material which is concentrated in isobutene in the bottom product from the second rectification column.

The objective is achieved in this manner.

Correspondingly, the described embodiments also provide a processing facility for the purification of isobutene from a C4 stream which contains at least 1-butene 2-butene, isobutane and isobutene. This facility comprises at least:

an isomerization reactor which comprises a catalyst which comprises at least one metal which is active in hydrogenation on a support, preferably an aluminium oxide support;
and
a rectification column which is connected downstream of the isomerization reactor.

The objective is also achieved in this manner.

Surprisingly, purified isobutene can be obtained using the process in accordance with the described embodiments which has a mass fraction of isobutene of at least 95%, preferably at least 98%, particularly preferably at least 99%.

A stream of material which is concentrated in isobutane and isobutene obtained from the C4 stream and a stream of hydrogen are supplied to the isomerization reactor which is preferably configured as disclosed in EP 2 170 494 B1, in order to catalytically isomerize the 1-butene present in the stream of material which is concentrated in isobutane and isobutene to 2-butene in the presence of hydrogen. In order to accelerate the isomerization, the isomerization reactor includes a catalyst which comprises at least one metal which is active in hydrogenation, on a support. The 1-butene from the stream of material which is concentrated in isobutane and isobutene is isomerized with hydrogen from the stream of hydrogen, in the presence of the catalyst in the isomerization reactor, to form 2-butene, in order to further reduce the proportion of 1-butene in the product stream from the isomerization reactor. This product stream is supplied to a rectification column, wherein a stream of material which is concentrated in isobutane is separated by distillation as the overhead product. There are four variations for obtaining a stream of material which is concentrated in isobutene from the rectification column. In the first, second or third variation, a stream of material which is concentrated in isobutene is obtained via a side stream, a side stream and as a bottom product, or as the bottom product from the rectification column. In the fourth variation, a stream of material which contains isobutane and isobutene is supplied, as the overhead product from the rectification column, to a second rectification column in order to separate the isobutane from the isobutene, and a stream of material which is concentrated in isobutane is obtained as the overhead product and a stream of material which is concentrated in isobutene as the bottom product from the second rectification column.

In accordance with a preferred embodiment, the C4 stream from which the stream of material which is concentrated in isobutane and isobutene is obtained is supplied to a further rectification column which is associated with a further catalyst which comprises at least one metal which is active in hydrogenation on a support, preferably on an aluminium oxide support. The C4 stream is separated by distillation in the further rectification column, whereupon a product stream containing 1-butene is obtained. The 1-butene which is contained in said product stream is isomerized to 2-butene by contact of this product stream with a further stream of hydrogen in the presence of the further catalyst. The metal which is active in hydrogenation of the further catalyst accelerates the reaction of 1-butene to 2-butene. The product from this catalytic reaction, the reaction product stream, is separated by distillation in the further rectification column. At least portions of the product streams obtained from this rectification (counter-current distillation) are again brought into contact with the hydrogen of the further stream of hydrogen in the presence of the further catalyst, in order to isomerize the 1-butene present in these product streams to 2-butene. The reaction product stream produced in this catalytic reaction is again separated by distillation in the further rectification column. This at least single repetition of the process steps of counter-current distillation and catalytic reaction guarantees that the concentration of 1-butene in the subsequent steps of the process will be low. A stream of material is separated from the bottom of the further rectification column which is concentrated in 2-butene from the C4 stream and from the catalytic isomerization of the 1-butene. The stream of material which is concentrated in isobutane and isobutene is separated from the further rectification column as the overhead product, and so the head of the further rectification column is connected to the isomerization reactor. The stream of material which is concentrated in isobutane and isobutene comprises less 1-butene and 2-butene compared with the C4 stream which is supplied to the further rectification column as the feed.

In accordance with a preferred embodiment, the processing facility comprises a further rectification column which is associated with a further catalyst that comprises at least one metal which is active in hydrogenation on a support, preferably on an aluminium oxide support, wherein the isomerization reactor is downstream of the head of the further rectification column.

In a preferred alternative embodiment, at least a portion of the further catalyst is located outside the further rectification column in a reactor, wherein the reactor is connected to the further rectification column by means of a connection that leads to it and a connection that leads from it. In this manner, a product stream containing 1-butene which is formed during the separation by distillation in the further rectification column, separated from the further rectification column via a side stream and supplied to the reactor via the connection that leads to it. In addition, the further stream of hydrogen is supplied to the reactor in order to provide the hydrogen required for the isomerization. The reaction product stream produced during the isomerization over the further catalyst is supplied to the further rectification column via the recycle connection and is separated therein by distillation.

In a further preferred alternative embodiment, the further catalyst in the further rectification column is provided in at least one separation stage of the further rectification column. In this regard, the C4 stream and the further stream of hydrogen are supplied to the further rectification column and a product stream containing 1-butene which is produced in the further rectification column during the separation by distillation is supplied to the further catalyst inside the further rectification column and the 1-butene of this product stream is isomerized to 2-butene in the presence of hydrogen. The reaction product stream produced inside the further rectification column during this catalytic isomerization is separated by distillation in the further rectification column.

In order to achieve a high purity for the isobutene obtained, advantageously, the mass fraction of the isobutene in the C4 stream which is supplied to the further rectification column is at least 10%, preferably at least 15%, in particular at least 20%.

Furthermore, for high purity of the isobutene obtained, advantageously, the mass fraction of the 1-butene in the C4 stream which is supplied to the further rectification column is a maximum of 40%, preferably a maximum of 30%, in particular a maximum of 25%.

Furthermore, for high purity of the isobutene obtained, advantageously, the mass fraction of 2-butene in the C4 stream which is supplied to the further rectification column is a maximum of 60%, preferably a maximum of 50%, in particular a maximum of 40%.

In order to particularly promote an isomerization of the 1-butene to 2-butene in relation to isomerization of the isobutene, advantageously, the temperature in the isomerization reactor is between 20° C. and 130° C., preferably between 30° C. and 80° C., in particular between 40° C. and 70° C.

In accordance with a preferred embodiment, the pressure in the isomerization reactor is between 3 bar and 30 bar, preferably between 5 bar and 20 bar, in particular between 7 bar and 16 bar, in order to particularly promote an isomerization of the 1-butene to 2-butene compared with isomerization of the isobutene.

In accordance with a further preferred embodiment, at least a portion of the stream of material which is concentrated in isobutane and isobutene is liquefied in a condenser of the further rectification column, in order to obtain a liquid phase or a mixed phase of this stream of material. Furthermore, advantageously, the isomerization reactor comprises a mixing and distributing device. Particular preferably, this mixing and distributing device is used to bring the stream of material which is concentrated in isobutane and isobutene from the further rectification column as the liquid phase or as a mixed phase and the stream of hydrogen as the gaseous phase into homogeneous contact with the catalyst of the isomerization reactor, in order to ensure as much mixing as possible of the stream of material which is concentrated in isobutane and isobutene with the stream of hydrogen. Mixing and distributing devices of this type have been known in the art for a long time, and so further details in this regard would be unnecessary.

In order to obtain a high degree of isomerization, advantageously, when supplied to the isomerization reactor, the flow rate of hydrogen per t/h of the stream of material which is concentrated in isobutane and isobutene is between 0.02 $Nm^3/h$ and 200 $Nm^3/h$, preferably between 0.1 $Nm^3/h$ and 50 $Nm^3/h$, in particular between 0.5 $Nm^3/h$ and 5 $Nm^3/h$. This ratio guarantees that 1-butene is isomerized to 2-butene at a high isomerization rate and the reaction rate for the side reaction of the isobutene with hydrogen to form isobutane is minimized.

In accordance with a preferred embodiment, the rectification column has between 100 and 220 separation stages, preferably between 120 and 200 separation stages, in particular between 130 and 180 separation stages. Furthermore, advantageously, the recycle-to-distillate recycle ratio for the rectification column is at least 10:1, preferably at least 15:1, in particular at least 20:1.

In order to increase the yield of purified isobutene for a constant C4 stream input, advantageously, at least a portion of the bottom product from the rectification column is supplied to the C4 stream as the recycle stream. To this end, the bottom of the rectification column is connected to the line which is provided for conveying the C4 stream which is fed into the further rectification column.

In accordance with a further preferred embodiment, the stream of material which is concentrated in isobutene which is obtained from the rectification column is supplied to an additional rectification column in order to obtain a further purified isobutene stream of material which comprises less 1-butene and 2-butene in comparison to the stream of material which is concentrated in isobutene. Particularly preferably, the mass fraction of isobutene in the further purified isobutene stream of material from the additional rectification column is at least 95%, preferably at least 98%, particularly preferably at least 99%, in particular at least 99.5%.

In order to keep the input from the C4 stream as low as possible, advantageously, at least a portion of the bottom product from the additional rectification column is supplied to the C4 stream as a recycle stream in order to increase the yield of purified isobutene for a constant C4 stream. To this end, the bottom of the additional rectification column is connected to the line which is provided for conveying the C4 stream, which is supplied to the further rectification column.

In accordance with a further preferred embodiment, the stream of material which is concentrated in isobutene is separated from the rectification column via a side stream, wherein between 8% and 25%, preferably between 10% and 20%, in particular between 12% and 15% of the total separation stages of the rectification column are below the separation stage in which the side stream is located. Particularly preferably, the mass fraction of the isobutene in this stream of material which is concentrated in isobutene is at least 95%, preferably at least 98%, particularly preferably at least 99%, in particular at least 99.5%.

In order to reduce the energy requirement, advantageously, the further rectification column is at a higher temperature than the rectification column and a heat exchanger is connected to the rectification column and to the further rectification column to exchange heat between the rectification column and the further rectification column, in order to supply the rectification column with heat from the further rectification column.

In accordance with a further preferred embodiment, the further catalyst is a PdO catalyst supported on $Al_2O_3$.

In accordance with a further preferred embodiment, the metal which is active in hydrogenation of the catalyst of the isomerization reactor is from group 8, 9 or 10 of the periodic table of the elements, in particular palladium or platinum. Particularly preferably, the metal which is active in hydrogenation of this catalyst is palladium with a mass fraction of between 0.01% and 5%, preferably between 0.1% and 0.7%, in particular between 0.2% and 0.5%.

In accordance with a particularly preferred embodiment, the aluminium oxide support of the catalyst for the isomerization reactor comprises spherical shaped articles.

In accordance with a further preferred embodiment, the aluminium oxide support of the catalyst for the isomerization reactor comprises extrudates or tablets.

BRIEF DESCRIPTION OF THE DRAWINGS

The described embodiments will now be described in more detail with the aid of the non-limiting exemplary embodiments shown in the drawings.

DETAILED DESCRIPTION

Figure 1:
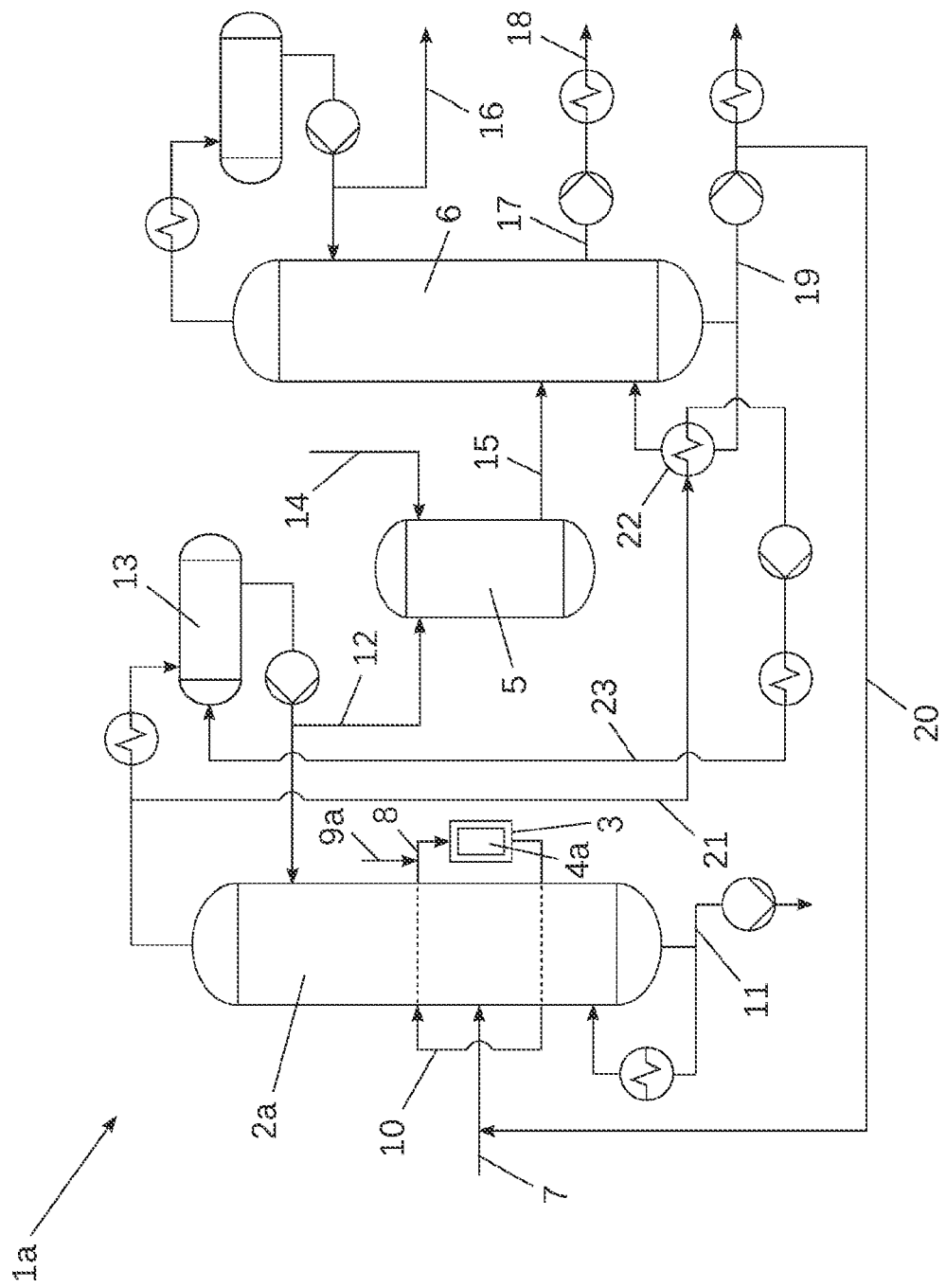
FIG. 1 shows a process flow diagram for a processing facility in accordant e with the described embodiments, in which isobutene from a C4 stream is purified.

FIG. 1 shows a process flow diagram for a facility 1 in accordance with the described embodiments which has an isomerization reactor 5, a rectification column 6, a further rectification column 2a and a reactor 3 which contains a further catalyst 4a. The farther catalyst 4a in reactor 3 and the further rectification column 2a serve for repeated isomerization and separation by distillation of 1-butene in a C4 stream, wherein the reactor 3, which comprises the further catalyst 4a for isomerization of 1-butene, is outside the further rectification column 2a. Processes for repeated isomerization and separation of 1-butene in a C4 stream by distillation in a rectification column and a catalyst at least a portion of which is outside the rectification column are known, for example from EP 0 922 018 B1.

In the embodiment illustrated in FIG. 1, a C4 stream 7, which may contain mass fractions of 10% to 40% isobutane, 10% to 20% isobutene, 4% to 10% 1-butene and 30% to 60% 2-butene, are fed continuously into the further rectification column 2a. In the further rectification column 2a, the C4 stream 7 is separated by distillation and a product stream 8 containing 1-butene formed in the further rectification column 2a is removed from the further rectification column 2a via at least one side stream. This product stream 8 is supplied continuously to a reactor 3 via a line together with a further stream of hydrogen 9a, wherein the reactor 8 is outside the further rectification column 2a and includes the farther catalyst 4a. The product stream 8 is supplied to the reactor 3 separately from the further hydrogen stream 9a; this product stream 8 may also be mixed with the further hydrogen stream 9a prior to being supplied to the reactor 3. In the reactor 3, the 1-butene which is in the product stream 8 reacts with the hydrogen of the further hydrogen stream 9a in the presence of the further catalyst 4a, which is a PdO catalyst supported on $Al_2O_3$, to form 2-butene. The reaction product stream 10 which is thus formed, which contains less 1-butene and more 2-butene than the product stream 8, is supplied again to the further rectification column 2a via a recycle line. In this regard, as can be seen in FIG. 1, feeding of the recycled reaction product stream 10 may be carried out in the same separation stage f the further rectification column 2a as the removal of the product stream 8. The bottom product from the further rectification column 2a is a stream of material 11 which is concentrated in 2-butene and the overhead product is a stream of material 12 which is concentrated in isobutane and isobutene, wherein this stream of material 12 contains less 1-butene and 2-butene compared with that of the C4 stream 7 supplied to the further rectification column 2a. The mass fractions of the stream of material 12 which is concentrated in isobutane and isobutene may, for example, be approximately 48% isobutane, approximately 50% isobutene, 600 to 1000 ppm 1-butene and 200 to 400 ppm 2-butene.

In the embodiment shown in FIG. 1, at least a portion of the overhead product from the further rectification column 2a, the stream of material 12 which is concentrated in isobutane and isobutene, is liquefied in a condenser 13 of the further rectification column 2a and is continuously supplied to an isomerization reactor 5 which is connected downstream of the head of the further rectification column 2a and is operatively connected to the further rectification column 2a. In this context, the term "operatively connected" means that during operation of the processing facility which comprises these parts of the facility, the isomerization reactor 5 and the further rectification column 2a are connected together in a manner such that an exchange of material and/or energy between the isomerization reactor 5 and the further rectification column 2a can take place. In addition, a stream of hydrogen 14 is supplied to the isomerization reactor 5. The stream of material 12 which is concentrated in isobutane and isobutene is supplied to the isomerization reactor 5 separately from the stream of hydrogen 14, wherein this stream of material 12 may also be mixed with the stream of hydrogen 14 prior to being supplied to the isomerization reactor 5. Per t/h of the stream of material 12 concentrated in isobutane and isobutene, between 0.5 $Nm^3/h$ and 5 $Nm^3/h$ of hydrogen is supplied to the isomerization reactor 5 via the stream of hydrogen 14. By means of this three-phase reaction of the stream of material 12 which is concentrated in isobutane and isobutene as the liquid phase, the stream of hydrogen 14 as the gaseous phase and the catalyst of the isomerization reactor 5 as the solid phase, a mixing and distributing device is present in the isomerization reactor 5 this is known, for example, from EP 2 170 494 B1—this is in order to obtain as great an amount of mixing of the reagents as possible. The mixing and distributing device comprises a trough distributor with trough-shaped channels and outlet tubes in the trough-shaped channels for the liquid phase and a distributor plate which is located below the trough distributor and has vertical nozzles. Furthermore, the isomerization reactor 5 comprises a catalyst with a horizontally disposed solid catalyst bed with spherical shaped articles, wherein the catalyst comprises at least one metal which is active in hydrogenation on an aluminium oxide support. The metal which is active in hydrogenation of this catalyst is palladium in a mass fraction of between 0.2% and 0.5%. The stream of material 12 which is concentrated in isobutane and isobutene as the liquid phase and the stream of hydrogen 14 as the gaseous phase are guided from top to bottom in a co-current process with the aid of the mixing and distributing device, over the solid catalyst bed of the catalyst through the isomerization reactor 5 in order to catalytically isomerize 1-butene present in the stream of material 12 which is concentrated in isobutane and isobutene with the aid of hydrogen to 2-butene. In this isomerization in the isomerization reactor 5, the temperature is between 40° C. and 70° C., and the pressure is between 7 bar and 16 bar.

In the embodiment shown in FIG. 1, the product stream 15 from the isomerization in the isomerization reactor 5 is supplied to a rectification column 6 which is connected downstream of the isomerization reactor 5 and is operatively connected to it. The rectification column 6 comprises between 130 and 180 separation stages and the recycle ratio of recycle to distillate is 20:1. In the rectification column 6, the product stream 15, which contains mass fractions of approximately 48% isobutane, approximately 50% isobutene, 100 to 200 ppm 1-butene and 700 to 1200 ppm 2-butene, is separated by distillation. In this regard, a stream of material which is concentrated in isobutane is separated from the rectification column 6 as the overhead product 16; it has a mass fraction of isobutane of 80% to 95% and a mass fraction of isobutene of 5% to 20%. The rectification column 6 has a side stream 17, wherein between 12% and 15% of the total separation stages of the rectification column 6 are below the separation stage in which the side stream 17 is located. A stream of material 18 which is concentrated in isobutene is separated via this side stream 17; it has mass fractions of 99.7% isobutene, 0.2% isobutane, 200 ppm of 1-butene and 400 ppm of 2-butene. The mass fraction of isobutene in the bottom product 19 from the rectification column 6 is approximately 98% and the mass fraction of 2-butene is approximately 2%. In the embodiment shown in FIG. 1, a proportion of the bottom product 19 is supplied to the C4 stream 7 as the recycle stream 20. In this regard, the bottom of the rectification column 6 and the line which is provided for feeding the C4 stream 7 into the further rectification column 2a are operatively connected together by means of a line for conveying the recycle stream 20.

In the embodiment shown in FIG. 1, a stream of material 21, which is a portion of the stream of material which is withdrawn overhead from the further rectification column 2a, is supplied to the heat exchanger which is the evaporator for the rectification column 6, in order to give up heat to the mixture to be vaporized in the bottom of the rectification column 6 via the heat exchanger 22. In order to supply heat from the evaporator of the rectification column 6, the further rectification column 2a is operated at a higher temperature and at a higher pressure than the rectification column 6. A line for conveying the stream of material 21 connects the head of the further rectification column 2a with the heat exchanger 22 of the rectification column 6. After releasing heat, a stream of material 23, which has a lower energy content than the stream of material 21, is supplied from the heat exchanger 22 to the condenser 13 of the further rectification column 2a, in order to recycle the stream of material removed from the head of the further rectification column 2a to the head of the further rectification column 2a for the purposes of heat transfer. Correspondingly, the heat exchanger 22 of the rectification column 6 and the condenser 13 of the further rectification column 2a are connected via a line for conveying the stream of material 23.

Figure 2:
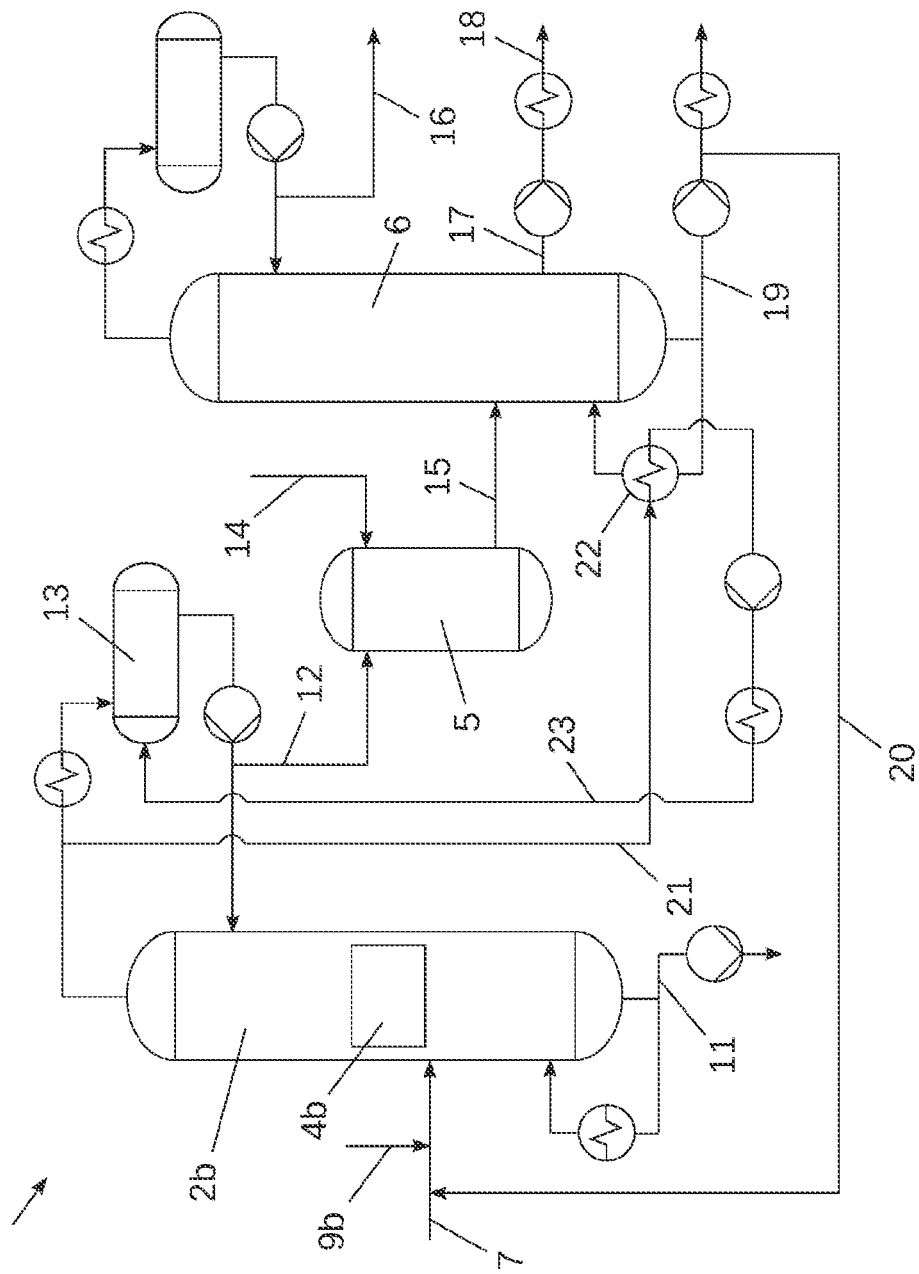
FIG. 2 shows a process flow diagram for a further embodiment of the processing facility.

FIG. 2 shows a process flow diagram for a further facility 1b in accordance with the described embodiments, which comprises a further rectification column 2b, a further catalyst 4b, the isomerization reactor 5 and the rectification column 6. The further catalyst 4b and the further rectification column 2b serve to carry out repeated isomerization and separation by distillation of 1-butene in a C4 stream, wherein the further catalyst 4b for isomerization of 1-butene is located within the further rectification column 2b in a separation stage. Processes for repeated isomerization and separation of 1-butene in a C4 stream by distillation with a rectification column and a catalyst which is located in the rectification column are known from EP 1 200 378 B1, for example.

In the embodiment shown in FIG. 2, prior to being fed into the further rectification column 2b, the C4 stream 7 is mixed with a further stream of hydrogen 9b and is then supplied to the further rectification column 2b. In addition to mixing the C4 stream 7 with the further stream of hydrogen 9b, separately supplying these two streams to the further rectification column 2b is also possible. In the further rectification column 2b, the C4 stream 7 is separated by distillation and the product stream 8 containing 1-butene formed in the further rectification column 2b is supplied, together with the hydrogen of the further stream of hydrogen 9h, to a further catalyst 4b, wherein the further catalyst 4b is located inside the further rectification column 2b in a separation stage. The product stream 8 is not shown in FIG. 2 because this corresponds to a stream of material in the further rectification column 2b which is located in the same separation stage as the further catalyst 4b and is brought into contact with this further catalyst 4b. In the presence of the further catalyst 4b, which is a PdO catalyst supported on $Al_2O_3$, the 1-butene which is in the product stream 8 reacts with the hydrogen of the further stream of hydrogen 9b in the further rectification column 2b to form 2-butene. The reaction product stream 10 formed in this manner, which contains less 1-butene and more 2-butene than the product stream 8, is also in the same separation stage as the further catalyst 4b and is separated by distillation in the further rectification column 2b. For this reason, the reaction product stream 10 is also not shown in FIG. 2. The bottom product from the further rectification column 2b is a stream of material 11 which is concentrated in 2-butene and the overhead product is a stream of material 12 which is concentrated in isobutane and isobutene, wherein this stream of material 12 has comparatively less 1-butene and 2-butene than that in the C4 stream 7 supplied to the further rectification column 2b, before this C4 stream 7 is mixed with the further stream of hydrogen 9b. The further steps of the process after the further rectification column 2b in the embodiment shown in FIG. 2 for obtaining a stream of material which is concentrated in isobutene are the same as the steps of the process after the further rectification column 2a in the embodiment of FIG. 1.

Figure 3:
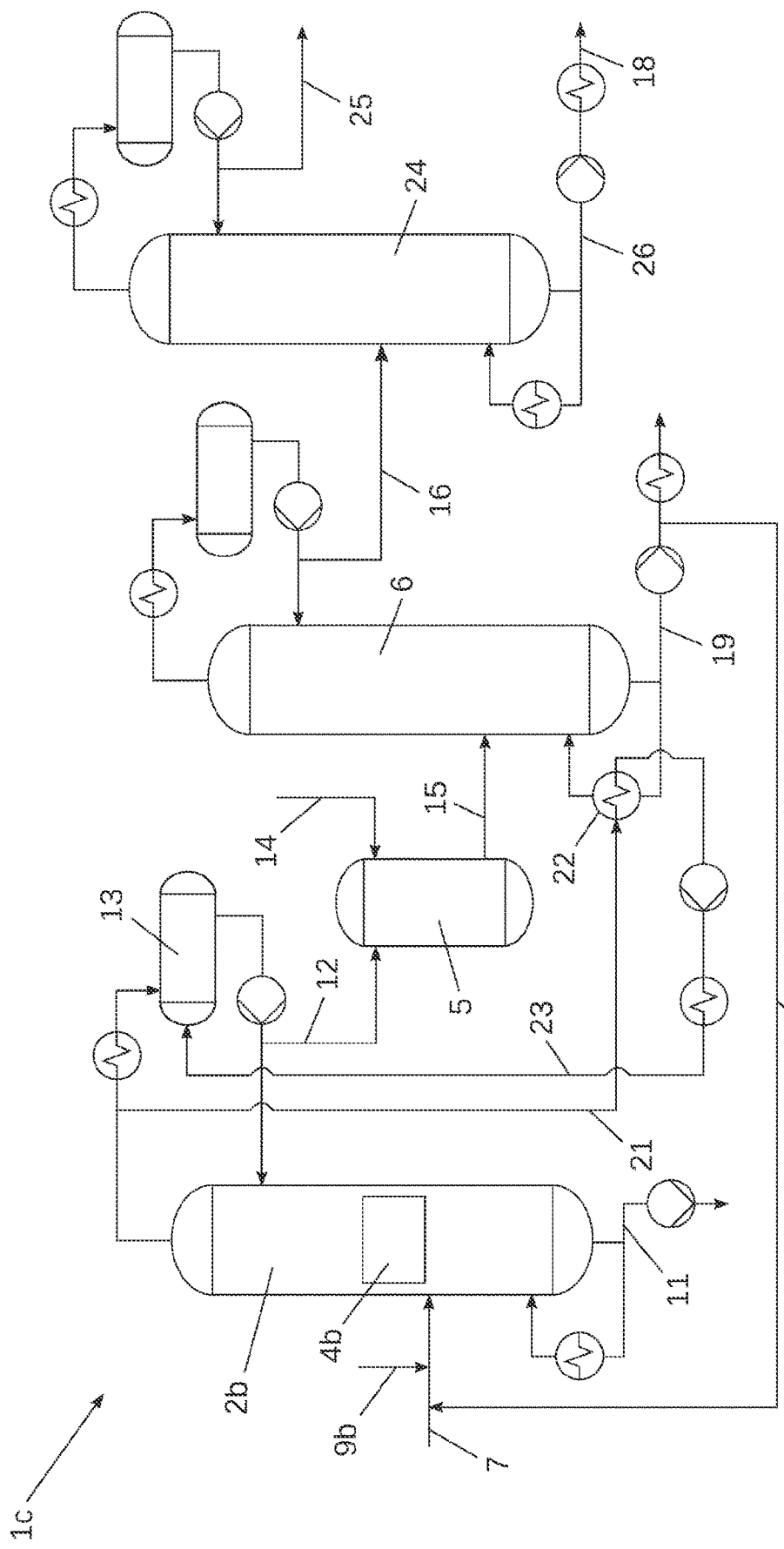
FIG. 3 shows a process flow diagram for a third embodiment of the processing facility.

FIG. 3 shows a process flow diagram for a further facility 1c in accordance with the described embodiments, which comprises the further rectification column 2b, the further catalyst 4b, the isomerization reactor 5 and the rectification column 6 in accordance with the alternative embodiment of FIG. 2. In contrast to the alternative embodiment of FIG. 2, the rectification column 6 in the embodiment shown in FIG. 3 does not have a side stream 17 for separation of a stream of material 18 which is concentrated in isobutene. The overhead product 16 from the rectification column 6 is supplied to a further rectification column 24 which is connected downstream of the head of the rectification column 6. For this reason, the head of the rectification column 6 and the second rectification column 24 are operatively connected to each other.

In the embodiment shown in FIG. 3, compared with the alternative embodiment of FIG. 2, the rectification column 6 is operated at a higher pressure and/or a higher temperature, so that a stream of material which is concentrated in isobutane and isobutene is separated from the rectification column 6 as the overhead product 16. This overhead product 16 is supplied to the second rectification column 24 in order to separate the isobutene from the isobutane and to obtain a stream of material which is concentrated in isobutane in the overhead product 25 and a stream of material 18 which is concentrated in isobutene in the bottom product 26 from the second rectification column 24. The mass fraction of isobutene in this stream of material 18 which is concentrated in isobutene is at least 99%.

Figure 4:
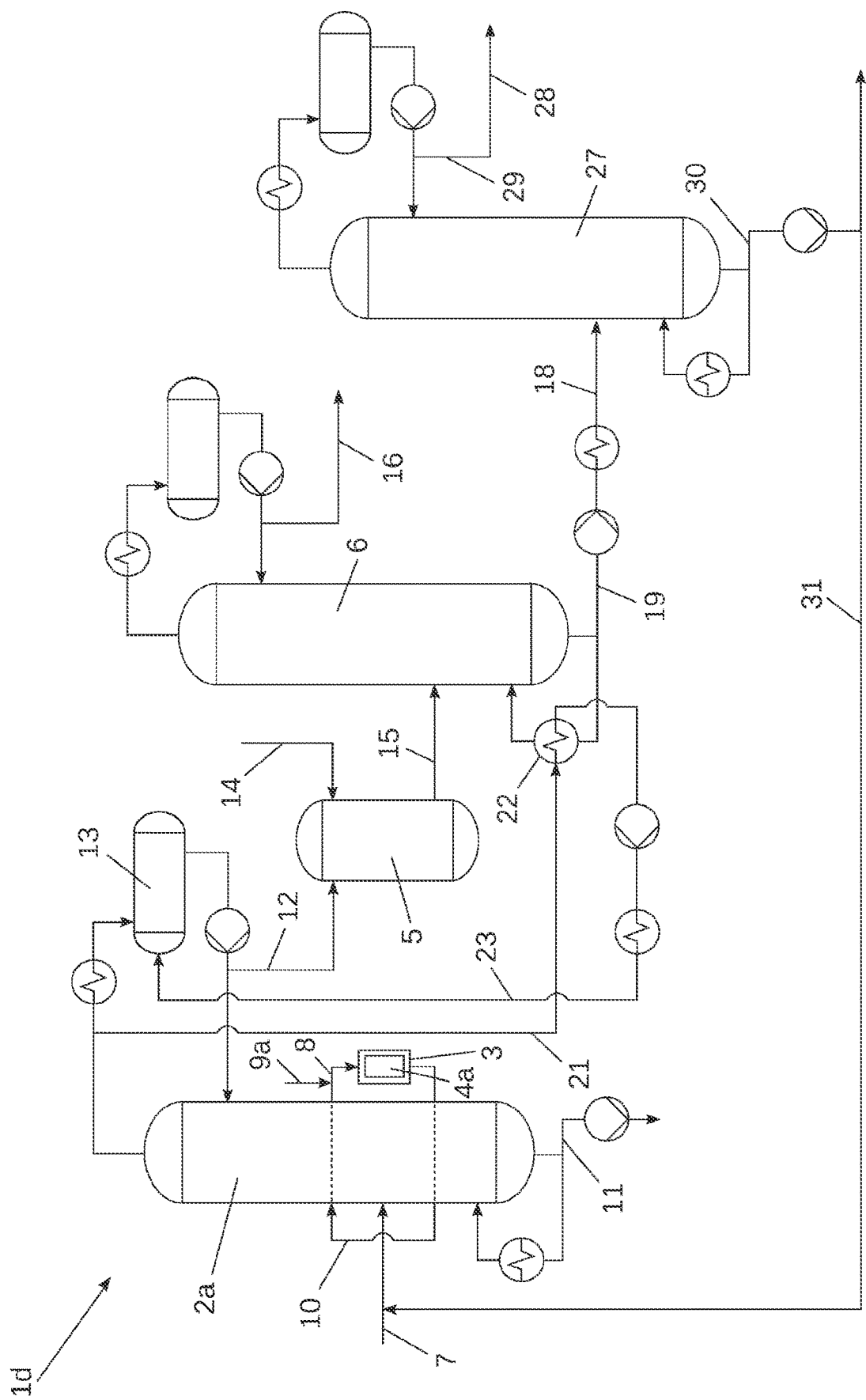
FIG. 4 shows a process flow diagram for a fourth embodiment processing facility.

FIG. 4 shows a process flow diagram for a further facility 1d in accordance with the described embodiments which comprises the further rectification column 2a, the reactor 3, which contains the further catalyst 4a, the isomerization reactor 5 and the rectification column 6 in accordance with the alternative embodiment of FIG. 1. In contrast to the alternative embodiment of FIG. 1, the rectification column 6 in the embodiment shown in FIG. 4 does not have a side stream 17 for separating a stream of material 18 which is concentrated in isobutene. The bottom product 19 from the rectification column 6 is supplied to an additional rectification column 27 which is connected downstream of the bottom of the rectification column 6. For this reason, the bottom of the rectification column 6 and the additional rectification column 27 are connected together operatively.

In the embodiment shown in FIG. 4, the stream of material 18 which is concentrated in isobutene is supplied to the additional rectification column 27 as the bottom product 19 from the rectification column 6. In the additional rectification column 27, the isobutene is separated from 2-butene from the stream of material 18 which is concentrated in isobutene and a further purified isobutene stream 28 is obtained from the additional rectification column 27 as the overhead product 29. The mass fraction of the isobutene in this further purified isobutene stream 28 is at least 99.7%. A portion of the bottom product 30 from the additional rectification column 27, which comprises isobutene and 2-butene, is supplied to the C4 stream 7 as a recycle stream 31. In this manner, the bottom of the additional rectification column 27 and the line which is provided for feeding the C4 stream 7 into the further rectification column 2a are connected together operatively via a line for conveying the recycle stream 31.

The invention claimed is:

1. A processing facility for the purification of isobutene from a C4 stream which contains at least 1-butene, 2-butene, isobutane and isobutene, comprising the following equipment:
- an isomerization reactor which comprises a catalyst which comprises at least one metal which is active in hydrogenation on a support, wherein the catalyst is configured to isomerize 1-butene to 2-butene;
- a rectification column which is connected downstream of the isomerization reactor, wherein the rectification column is configured to produce a stream concentrated in isobutene;
- a further rectification column configured to receive the C4 stream and to produce a stream concentrated in 2-butene from a bottom of the further rectification column and a stream concentrated in isobutane and isobutene from a head of the further rectification column;
- a further catalyst that comprises at least one metal which is active in hydrogenation on a support, wherein the further rectification column is connected to the further catalyst at a point below the head and above the bottom of the further rectification column, wherein the further catalyst is configured to isomerize 1-butene to 2-butene, and wherein the isomerization reactor is downstream of the head of the further rectification column;
- a heat exchanger configured to provide heat to the rectification column; and
- a line which is connected to the head of the further rectification column and to the heat exchanger for heat transfer between the rectification column and the further rectification column.

2. The processing facility as claimed in claim 1, wherein the rectification column comprises a side stream for separating a stream of material containing isobutene.

3. The processing facility as claimed in claim 1, wherein the support is an aluminium oxide support.

4. A processing facility for the purification of isobutene from a C4 stream which contains at least 1-butene, 2-butene, isobutane and isobutene, comprising the following equipment:
- an isomerization reactor which comprises a catalyst which comprises at least one metal which is active in hydrogenation on a support, wherein the catalyst is configured to isomerize 1-butene to 2-butene;
- a rectification column which is connected downstream of the isomerization reactor, wherein the rectification column is configured to produce a stream concentrated in isobutene;
- a further rectification column configured to receive the C4 stream and to produce a stream concentrated in 2-butene from a bottom of the further rectification column and a stream concentrated in isobutane and isobutene from a head of the further rectification column;
- a further catalyst that comprises at least one metal which is active in hydrogenation on a support, wherein the further rectification column is connected to the further catalyst at a point below the head and above the bottom of the further rectification column, wherein the further catalyst is configured to isomerize 1-butene to 2-butene, and wherein the isomerization reactor is downstream of the head of the further rectification column; and
- a line configured to provide a C4 stream containing at least 1-butene, 2-butene, isobutane and isobutene into the further rectification column, wherein a bottom of the rectification column is connected to the line provided to convey the C4 stream for at least partial recycling of the bottom product from the rectification column.

* * * * *